US00PP30043P3

(12) United States Plant Patent
Eveleens

(10) Patent No.: US PP30,043 P3
(45) Date of Patent: Jan. 1, 2019

(54) ***HYDRANGEA* PLANT NAMED 'HORTMAMORE'**

(50) Latin Name: *Hydrangea macrophylla*
Varietal Denomination: Hortmamore

(71) Applicants: Horteve Breeding BV, Aalsmeer (NL); Kolster Holding BV, Boskoop (NL)

(72) Inventor: Cornelis Pieter Eveleens, Aalsmeer (NL)

(73) Assignees: HORTEVE BREEDING B.V., Aalsmeer (NL), part interest; KOLSTER HOLDING B.V., Boskoop (NL), part interest ( * ) Notice: Subject to any disclaimer, the term of this patent is extended or adjusted under 35 U.S.C. 154(b) by 0 days.

(21) Appl. No.: 15/731,902

(22) Filed: Aug. 21, 2017

(65) Prior Publication Data

US 2018/0184560 P1 Jun. 28, 2018

(30) Foreign Application Priority Data

Dec. 22, 2016 (QZ) ..... PBR 2016/3258

(51) Int. Cl.
*A01H 5/00* (2018.01)
*A01H 5/02* (2018.01)

(52) U.S. Cl.
USPC ..... Plt./250
CPC ..... *A01H 5/02* (2013.01)

(58) Field of Classification Search
USPC ..... Plt./250
See application file for complete search history.

*Primary Examiner* — Susan McCormick Ewoldt
(74) *Attorney, Agent, or Firm* — Penny J. Aguirre

(57) ABSTRACT

A new cultivar of *Hydrangea macrophylla* plant named 'Hortmamore' that is characterized by its exhibits mophead type inflorescences with sterile flower sepals that are bright red in color, its sturdy and thick textured sterile flower sepals, its good performance both as a cut flower and as a potted plant, and its floriferous blooming habit.

2 Drawing Sheets

Botanical classification: *Hydrangea macrophylla.*
Varietal denomination: 'Hortmamore'.

CROSS REFERENCE TO A RELATED APPLICATION

This application is co-pending with a U.S. Plant patent applications filed for a plant derived from the same breeding program that is entitled *Hydrangea* Plant Named 'Hortmalegretto' (co-pending U.S. Plant patent application Ser. No. 15/731,893) and *Hydrangea* Plant Named 'Hortmagitri' (co-pending U.S. Plant patent application Ser. No. 15/731,894).

BACKGROUND OF THE INVENTION

The present invention relates to a new and distinct cultivar of *Hydrangea macrophylla* and will be referred to hereafter by its cultivar name, 'Hortmamore'. 'Hortmamore' represents a new big leaf *hydrangea*, a perennial shrub grown for use as a landscape plant and for cut flower production.

'Hortmamore' was derived from an ongoing controlled breeding program directed by the Inventor in Boskoop, The Netherlands. The objective of the breeding program was to develop new cultivars of *Hydrangea* with flowers that are red in color with sturdy and thick textured sterile sepals combined with floriferous blooming habits. 'Hortmamore' arose from a controlled cross made by the Inventor in June of 2010 between unnamed and unpatented proprietary plants in the Inventor's breeding program; reference no. 08-007-02 as the female parent and *Hydrangea macrophylla* 'Kolmaru' (U.S. Plant Pat. No. 25,104) as the male parent. 'Hortmamore' was selected as a single unique plant from amongst the resulting seedlings in August of 2014.

Asexual propagation of the new cultivar was first accomplished by stem cuttings by the Inventor in Boskoop, The Netherlands in August of 2012. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hortmamore' as a unique cultivar of *Hydrangea macrophylla.*

1. 'Hortmamore' exhibits mophead type inflorescences with sterile flower sepals that are bright red in color.
2. 'Hortmamore' exhibits sturdy and thick textured sterile flower sepals.
3. 'Hortmamore' exhibits good performance both as a cut flower and as a potted plant.
4. 'Hortmamore' exhibits a floriferous blooming habit.

The female parent of 'Hortmamore' differs from 'Hortmamore' in having sterile flower sepals that are dark pink in color and softer in texture. The male parent of 'Hortmamore' differs from 'Hortmamore' in having sterile flower sepals that are darker red in color with a softer texture, and in having weaker flower stems. 'Hortmamore' can be most closely compared to the 'Hortmalegretto' and 'Hortmagitri'. These cultivars are similar to 'Hortmamore' in having sterile flower sepals that are red in color and thick textured. 'Hortmalegretto' differs from 'Hortmamore' in being less floriferous. 'Hortmagitri' differs from 'Hortmamore' in being less floriferous and in having sterile sepals that are darker red in color with even darker red markings, especially when the flowers are mature.

BRIEF DESCRIPTION OF THE DRAWINGS

The accompanying colored photographs illustrate the overall appearance and distinct characteristics of the new *Hydrangea*. The photographs were taken of a plant two years in age as grown in a 17-cm container in a greenhouse in Boskoop, The Netherlands.

The photograph in FIG. 1 provides a side view of the plant habit of 'Hortmamore' in bloom.

Figure 1:
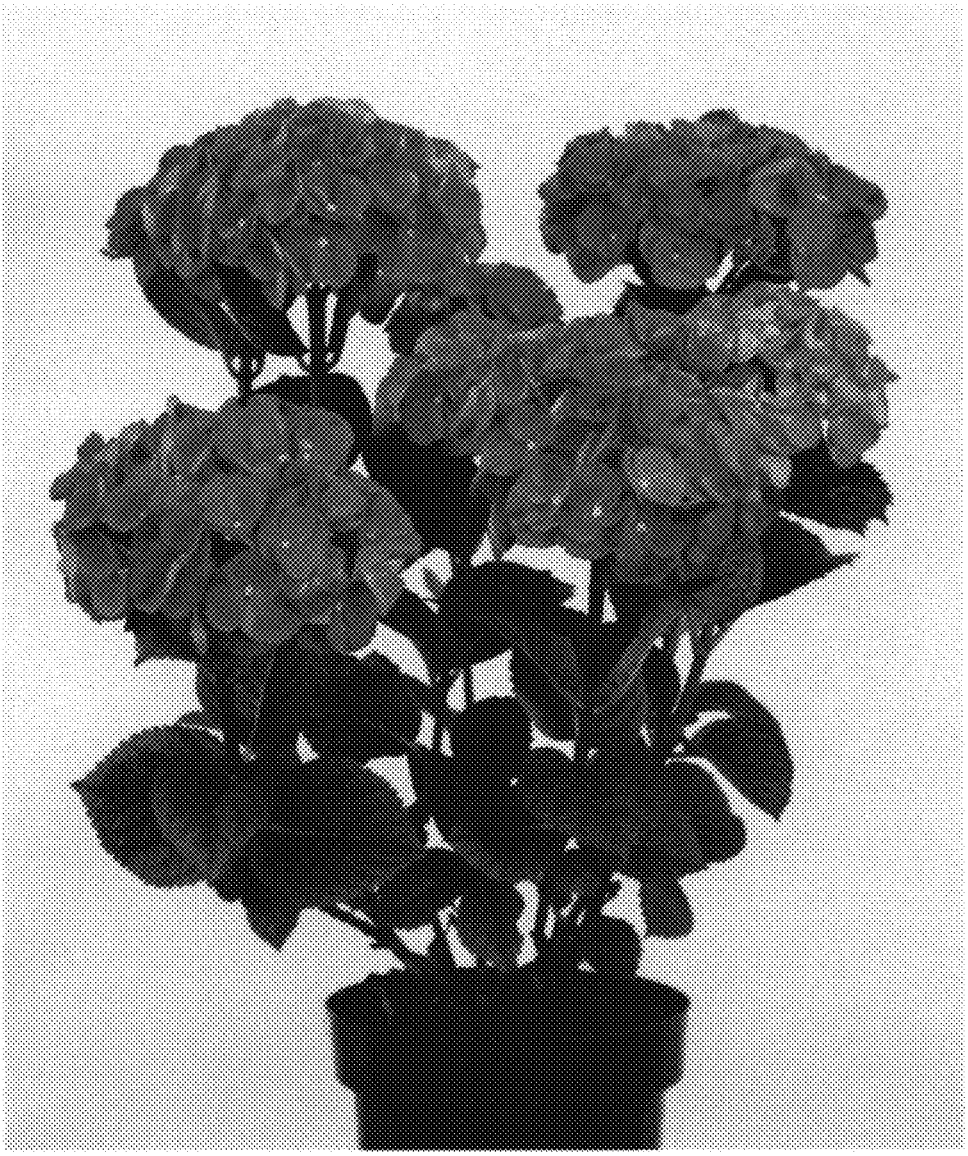
Figure 2:
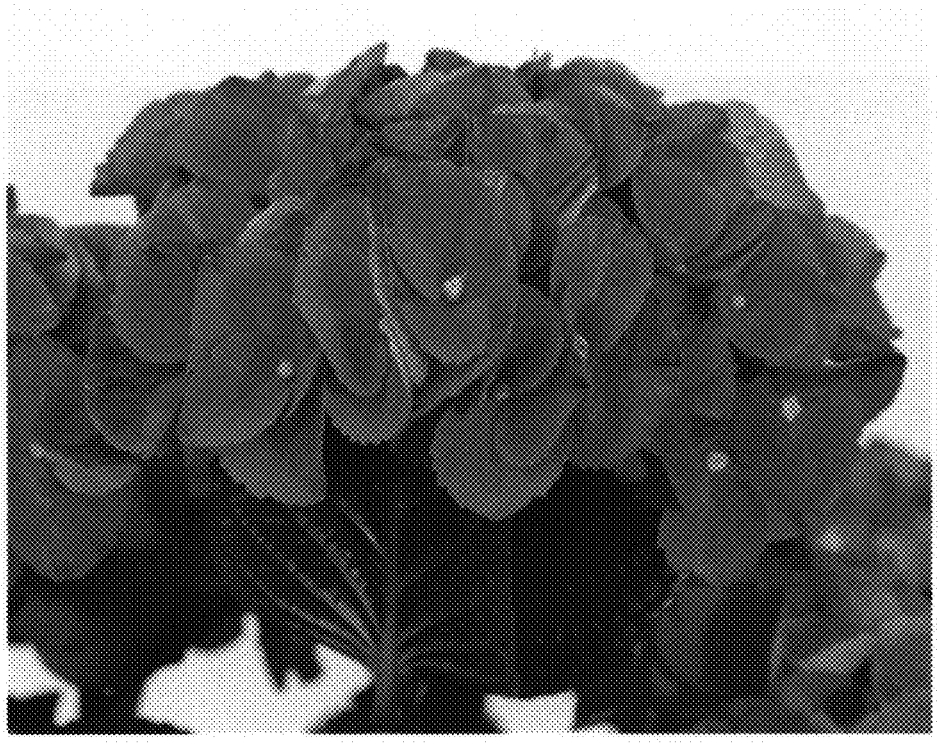

The photograph in FIG. 2 provides a close-up view of an inflorescence of 'Hortmamore'.

Figure 3:
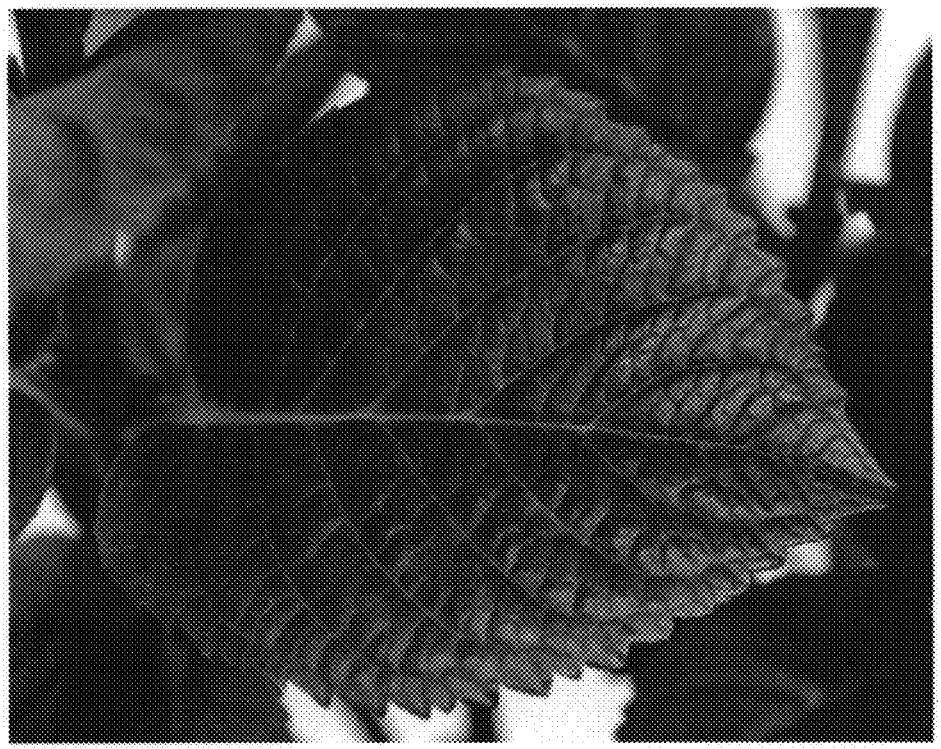

The photograph in FIG. 3 provides a close-up view a leaf of 'Hortmamore'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of plants two years in age as grown in 17-cm containers in a greenhouse in Boskoop, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—From late summer to fall and showy for at least to weeks in The Netherlands.

*Plant type*.—Perennial shrub, mophead type *Hydrangea*.

*Plant habit*.—Broadly spreading to upright.

*Height and spread*.—An average of 46 cm in height and 41 cm in spread as grown in a 17-cm container and about 1 m in height and width as a 3 year-old plant in the landscape.

*Hardiness*.—At least in U.S.D.A. Zones 5 to 9.

*Diseases and pests*.—No susceptibility or resistance to pests and diseases has been observed.

*Root description*.—Fibrous and fine, 199D in color.

*Propagation*.—Stem cuttings.

*Time required for root development*.—An average of 3.5 weeks for root initiation with a young rooted plant produced in an average of six months.

*Growth rate*.—Moderate.

Stem description:

*Stem shape*.—Rounded.

*Stem strength*.—Strong.

*Stem aspect*.—Upright to an average angle of 60° to soil.

*Stem color*.—Immature stems; 143A, mature stems; 144A, flushed with 143A at the internodes, older bark; N199B to N200A.

*Stem size*.—An average of 23 cm (excluding the inflorescence) in length and 6.5 mm in diameter.

*Stem surface*.—Immature and mature stems; glabrous and sparsely lenticellate with lenticels; an average of 1.5 mm in length, 0.5 mm in width, N186B in color.

*Branching*.—Freely branched with an average of 8 lateral branches, branching improves with pinching.

*Internode length*.—An average of 5.9 cm.

Foliage description:

*Leaf shape*.—Broad ovate.

*Leaf arrangement*.—Opposite.

*Leaf division*.—Simple.

*Leaf number*.—An average of 10 (5 pairs) per lateral branch.

*Leaf base*.—Truncate.

*Leaf apex*.—Apiculate.

*Leaf margins*.—Serrate-dentate.

*Leaf venation*.—Pinnate, color; upper surface 144B, lower surface 145B.

*Leaf size*.—An average of 9 cm in length and 7.8 cm in width.

*Leaf attachment*.—Petiolate.

*Leaf surface*.—Upper and lower surfaces; smooth and moderately rugose.

*Leaf color*.—Young leaves upper surface 139A, young lower surface 138A, mature upper surface between NN137A and 147A, mature lower surface between 138A and 147B.

*Petioles*.—An average of 1.1 cm in length and 3.5 mm in diameter, strong, color; upper surface 144A, lower surface 143B, upper surface texture is smooth and slightly glossy, lower surface texture is smooth and moderately glossy.

*Inflorescence type*.—Flattened globular, mophead type, compound corymb of rotate-shaped sterile flowers over fertile flowers.

*Lastingness of inflorescence*.—Sterile flowers; an average of 6 weeks, persistent, fertile flowers; an average of one week, self-cleaning.

*Lastingness as a cut flower*.—About 2 weeks in full color, longer as a drying inflorescence.

*Inflorescence number*.—One per lateral stem.

*Inflorescence size*.—An average of 8.4 cm in height and 15.7 cm in diameter.

*Flower number*.—An average of 55 sterile flowers and 22 fertile flowers per inflorescence.

*Flower fragrance*.—None.

*Flower aspect*.—Sterile flowers; upright, outwards, and slightly drooping, fertile flowers; upright.

*Flower size*.—Sterile flowers; an average of 4 cm in diameter and 1.9 cm in depth, fertile flowers; an average of 8 mm in diameter and 4 mm in depth.

*Flower shape*.—Sterile flowers; rotate, cup-shaped, fertile flowers; rotate, petals drop when mature.

*Flower buds*.—Sterile flowers; an average of 2.75 mm in length, 3 mm in diameter, globular in shape, color; 147D, top is flushed with 153D, fertile flowers; an average of 5 mm in length and 4 mm in diameter, obovate in shape, color; 150C, top flushed with 63C.

*Peduncles*.—An average of 7 cm in length and 7 mm in diameter, held upright to outwards, 144A in color, smooth surface, strong.

*Pedicels*.—Sterile flowers; an average of 1.8 cm in length and 2 mm in diameter, held at an average angle of 40° to peduncle, 63B in color, moderate strength, dull surface is moderately covered with thin hairs; an average of 0.2 mm in length and too small to measure color, fertile flowers; an average of 3 mm in length and 1 mm in diameter, held at an average angle of 15° to vertical, 63C in color, moderate strength, dull surface.

*Petals*.—Sterile flowers; average of 4, rotate, ovate in shape, concave, acute apex, cuneate base, entire margin, an average of 4 mm in length and 3 mm in width, glabrous and dull upper and lower surfaces, color when opening upper surface N74C, color when opening lower surface 63B, color when fully open upper surface N74C, color when fully open lower surface 63B to 63C, fertile flowers; average of 4, occasionally 5, rotate, ovate in shape, concave, acute apex, cuneate base, entire margin, an average of 4 mm in length and 2.75 mm in width, glabrous and dull upper and lower surfaces, color when opening and fully open upper surface N74C, color when opening and fully open lower surface 64D.

*Sepals*.—Sterile flowers; an average of 4, occasionally 3, rotate with pairs alternate in arrangement, broadly reniform to rhomboidal to broadly ovate in shape, apex is obtuse to emarginate, truncate base, margin irregularly dentate, an average of 2.6 cm in length and 3.7 cm in width, color; upper surface when opening 60A to 60B, fading to N57B at the base, lower surface when opening 63C, fading to 63B at the top, upper surface when fully open 59A, lower surface when fully open between 59D and 63B, upper surface fading to 59A, strongly flushed with N186A, lower surface fading to 147B, strongly flushed with 197A to 197B, both surfaces glabrous and dull, fertile flowers; an average of 6, rotate in arrangement, broadly ovate in shape, acute apex, broadly cuneate base, entire margin, an average of 1.75 mm in length and width, color when opening and fully open upper and lower surface 147D, flushed with 59D, tip 146B.

Reproductive organs:

*Gynoecium*.—Sterile flowers; 3 pistils, an average of 1 mm in length, stigma; club-shaped and 155D in color, style; 0.5 mm in length, 155D in color, ovary is 155A in color, fertile flowers; an average of 3 pistils, an average of 1 mm in length, stigma; club-shaped and 155D in color, style; 0.5 mm in length, 155D in color, ovary is 151D in color.

*Androecium*.—Sterile flowers; an average of 8 stamens, filaments; an average of 2.5 mm in length and NN155B in color, anthers; oblong in shape, an average of 1 mm in length and 155A in color, pollen; moderate in quantity, 159D in color, fertile flowers; an average of 10 stamens, filaments; an average of 3 mm in length and NN155D in color, anthers; oblong in shape, an average of 1 mm in length and 155A in color, pollen; moderate in quantity, 159D in color.

*Fruit and seed*.—No seeds or fruit observed.

It is claimed:

1. A new and distinct cultivar of *Hydrangea* plant named 'Hortmamore' substantially as herein illustrated and described.

* * * * *